US011103524B2

(12) United States Patent
Derrieu et al.

(10) Patent No.: US 11,103,524 B2
(45) Date of Patent: Aug. 31, 2021

(54) COMPOSITIONS FOR ORAL ADMINISTRATION TO ANIMALS, PROCESSES FOR OBTAINING THE SAME AND THE USES THEREOF

(75) Inventors: Guy Derrieu, Cagnes-sur-Mer (FR); Giancarlo Mazzola, Bedano (CH)

(73) Assignee: Friulchem Spa, Vivaro (IT)

( * ) Notice: Subject to any disclaimer, the term of this patent is extended or adjusted under 35 U.S.C. 154(b) by 318 days.

(21) Appl. No.: 14/344,246

(22) PCT Filed: Aug. 31, 2012

(86) PCT No.: PCT/EP2012/067005

§ 371 (c)(1), (2), (4) Date: Jun. 10, 2014

(87) PCT Pub. No.: WO2013/037650

PCT Pub. Date: Mar. 21, 2013

(65) Prior Publication Data

US 2014/0343004 A1 Nov. 20, 2014

(30) Foreign Application Priority Data

Sep. 15, 2011 (WO) ................ PCT/EP2011/065990

(51) Int. Cl.

| | |
|---|---|
| *A61K 31/7048* | (2006.01) |
| *A23K 40/25* | (2016.01) |
| *A23K 20/184* | (2016.01) |
| *A23K 20/168* | (2016.01) |
| *A23P 30/00* | (2016.01) |
| *A23K 40/20* | (2016.01) |
| *A23K 10/20* | (2016.01) |
| *A23K 10/30* | (2016.01) |
| *A23K 20/174* | (2016.01) |
| *A23K 20/158* | (2016.01) |
| *A23K 20/163* | (2016.01) |
| *A23K 20/10* | (2016.01) |
| *A23K 20/195* | (2016.01) |
| *A23K 20/20* | (2016.01) |
| *A23K 50/20* | (2016.01) |
| *A23K 50/40* | (2016.01) |
| *A61K 9/00* | (2006.01) |
| *A61K 31/722* | (2006.01) |
| *A61K 31/737* | (2006.01) |
| *A61K 31/4985* | (2006.01) |
| *A61K 31/506* | (2006.01) |
| *A61K 31/365* | (2006.01) |
| *A61K 31/505* | (2006.01) |
| *A61K 47/02* | (2006.01) |

(Continued)

(52) U.S. Cl.

CPC .......... *A61K 31/7048* (2013.01); *A23K 10/20* (2016.05); *A23K 10/30* (2016.05); *A23K 20/10* (2016.05); *A23K 20/158* (2016.05); *A23K 20/163* (2016.05); *A23K 20/168* (2016.05); *A23K 20/174* (2016.05); *A23K 20/184* (2016.05); *A23K 20/195* (2016.05); *A23K 20/30* (2016.05); *A23K 40/20* (2016.05); *A23K 40/25* (2016.05); *A23K 50/20* (2016.05); *A23K 50/40* (2016.05); *A23P 30/00* (2016.08); *A61K 9/0056* (2013.01); *A61K 31/365* (2013.01); *A61K 31/4985* (2013.01); *A61K 31/505* (2013.01); *A61K 31/506* (2013.01); *A61K 31/722* (2013.01); *A61K 31/737* (2013.01); *A61K 47/02* (2013.01); *A61K 47/10* (2013.01); *A61K 47/12* (2013.01); *A61K 47/14* (2013.01); *A61K 47/26* (2013.01); *A61K 47/42* (2013.01); *A61K 47/44* (2013.01); *A61K 47/46* (2013.01)

(58) Field of Classification Search

CPC .............. A61K 31/7048; A61K 31/506; A61K 31/4985; A23K 1/17

USPC .......... 514/30, 23, 25; 536/4.1, 123.13, 1.11

See application file for complete search history.

(56) References Cited

U.S. PATENT DOCUMENTS 3,037,911 A 6/1962 Stoyle et al.
5,380,535 A 1/1995 Geyer et al.
(Continued)

FOREIGN PATENT DOCUMENTS

AU 2001279664 B2 3/2006
DE 19853729 A1 3/2000
(Continued)

OTHER PUBLICATIONS

Oct. 17, 2012—International Search Report received in corresponding Application No. PCT/EP2012/067005.

*Primary Examiner* — Shaojia A Jiang
*Assistant Examiner* — Michael C Henry
(74) *Attorney, Agent, or Firm* — Banner & Witcoff, Ltd.

(57) ABSTRACT

The present invention concerns a solid, palatable composition and its preparation process which, relative to the total weight of the composition, comprises:

5 to 30%, preferably 8 to 20% by weight of at least one fat chosen from among a liquid oil, a fat, wax or mixture thereof, the liquid oil not to represent more than 8% by weight of the composition;

0.001 to 85% by weight of at least one active substance; and 20 to 95%, preferably 40 to 70% by weight of at least one palatable material, for use thereof as medicinal product, nutraceutical or food supplement, for oral administration to mammals, except man, in particular for domestic animals such as dogs, cats or horses.

The said solid composition is obtained by mixing the components, vaporising the fats, calibrating the dry, fluid granular material and compressing the granular material in a stock cube press.

30 Claims, 2 Drawing Sheets

(51) Int. Cl.

| | |
|---|---|
| ***A61K 47/10*** | (2017.01) |
| ***A61K 47/12*** | (2006.01) |
| ***A61K 47/14*** | (2017.01) |
| ***A61K 47/26*** | (2006.01) |
| ***A61K 47/42*** | (2017.01) |
| ***A61K 47/44*** | (2017.01) |
| ***A61K 47/46*** | (2006.01) |

(56) References Cited

U.S. PATENT DOCUMENTS 5,637,313 A 6/1997 Chau et al.
5,674,515 A 10/1997 Wesenhagen
5,762,922 A * 6/1998 Noble .................. A61K 31/195 424/85.1
5,792,470 A 8/1998 Baumgardner, Sr.
5,853,757 A 12/1998 Durand et al.
5,894,029 A 4/1999 Brown et al.
6,126,979 A 10/2000 Herreid et al.
6,143,316 A 11/2000 Hayden et al.
6,455,083 B1 9/2002 Wang
6,716,456 B1 * 4/2004 Mapelli .................... B01J 13/10 424/400
7,431,941 B2 * 10/2008 Besins ................. A61K 9/4858 424/456
2002/0022640 A1 * 2/2002 Zeldis ................ A61K 31/4458 514/317
2004/0037869 A1 2/2004 Cleverly et al.
2004/0043925 A1 3/2004 Kalbe et al.
2004/0151759 A1 8/2004 Cleverly et al.
2005/0220869 A1 * 10/2005 Stroppolo ............ A61K 9/0056 424/464
2005/0226908 A1 10/2005 Huron et al.
2006/0182691 A1 * 8/2006 Besse ..................... A61K 9/143 424/46
2007/0128251 A1 * 6/2007 Paulsen ................ A61K 9/0056 424/439
2008/0160067 A1 7/2008 Boeckh et al.
2008/0166459 A1 * 7/2008 Achterkamp ............. A23L 1/40 426/249
2009/0280159 A1 11/2009 Paulsen et al.
2010/0022469 A1 * 1/2010 Razzak .................. A01N 43/90 514/53
2011/0009347 A1 * 1/2011 Liang ................... A61K 31/155 514/23
2011/0028436 A1 * 2/2011 Greenwald .......... A61K 31/122 514/89
2011/0183036 A1 7/2011 Teconchuk et al.
2012/0141574 A1 6/2012 Paulsen et al.

FOREIGN PATENT DOCUMENTS

| | | | |
|---|---|---|---|
| EP | 0320320 | A2 | 6/1989 |
| EP | 0574301 | A1 | 12/1993 |
| EP | 0725570 | A1 | 8/1996 |
| EP | 0725627 | A1 | 8/1996 |
| EP | 0997143 | A2 | 5/2000 |
| EP | 1490037 | A1 | 12/2004 |
| FR | 2154424 | A1 | 5/1973 |
| FR | 2350105 | A1 | 12/1977 |
| FR | 2709420 | A1 | 3/1995 |
| FR | 2715803 | A1 | 8/1995 |
| FR | 2896958 | A1 | 8/2007 |
| GB | 2432506 | A | 5/2007 |
| IE | 20040393 | A1 | 3/2005 |
| OA | 12967 | A | 10/2006 |
| WO | 98/12442 | A1 | 3/1998 |
| WO | 01/15547 | A2 | 3/2001 |
| WO | 03/030863 | A1 | 4/2003 |
| WO | 2004/043427 | A1 | 5/2004 |
| WO | 2004/112513 | A1 | 12/2004 |
| WO | 2005/13714 | A1 | 2/2005 |
| WO | 2006/063694 | A1 | 6/2006 |
| WO | 2007/085609 | A1 | 8/2007 |
| WO | 2007/090987 | A2 | 8/2007 |
| WO | 2008/030469 | A2 | 3/2008 |
| WO | 2009/064859 | A1 | 5/2009 |
| WO | 2009/068378 | A1 | 6/2009 |
| WO | 2012/049156 | A1 | 4/2012 |

* cited by examiner

COMPOSITIONS FOR ORAL ADMINISTRATION TO ANIMALS, PROCESSES FOR OBTAINING THE SAME AND THE USES THEREOF

RELATED APPLICATION DATA

This application is a National Stage Application under 35 U.S.C. 371 of co-pending PCT application PCT/EP2012/067005 designating the United States and filed Aug. 31, 2012; which claims the benefit of PCT application number PCT/EP2011/065990 and filed Sep. 15, 2011 each of which are hereby incorporated by reference in their entireties.

The present invention relates to the field concerning the preparing of palatable compositions for therapeutic purposes, more particularly to improve oral administration and to guarantee treatment compliance, that are formulated in solid form for animals (domestic, bred or wild).

At the current time developments are being seen in the care given to animals, and the oral route is becoming a priority route for administering medications by health professionals or owners, this being particularly true for nutraceutical products. The usual route for parenteral administration of medications in particular (intramuscular, subcutaneous, intradermal or intravenous), have a number of drawbacks. For example the intramuscular or sub-cutaneous routes may be the cause of haematomas or abscesses. The intravenous route often requires the services of a specialist (veterinary surgeon). As for the intradermal route this requires the use of solvents to allow the active molecules to pass through the skin barrier. These parenteral routes of administration also require the restraining of animals. In addition, some active substances are difficult to formulate in parenteral dosage forms. Finally, some active substances only exert their therapeutic action in animals if they can arrive directly in the digestive tract. For compositions to be accepted by an animal, they must be palatable so that they can be absorbed, after which animal satisfaction will be seen as the demanding for more. It is this satisfaction that is sought after and will be highly appreciated by animal owners.

It is known that the natural acceptance and consumption of a composition by an animal is based on two main characteristics of the dosage form: palatability and texture of the composition, and to a lesser extent the shape and size thereof.

Two other parameters must be added thereto:

full control over the quantity of one or more active substances, whether the composition is a medication, nutraceutical or food supplement, and the cost of the composition, in particular if it is a nutraceutical or food supplement.

The dose formulations adapted for administering compositions via oral route or per os are generally in liquid form (e.g. syrups, solutions or drinkable suspensions, drops . . . ), in semi-solid form (e.g. pastes for oral administration) or solid form. The solid forms frequently used per os for the animal population are in various formulations of different type and obtained using different methods. For example a distinction is made between tablets, pills, hard capsules, soft capsules, chewable gums, pellets . . . . It has chiefly been ascertained, for heed of treatment via oral route (i.e. heed of directions and recommendations given by the health professional for the taking of medication) that treatment is not always properly followed on account of the difficulty in administering treatments in full to animals. The administering of medications to animals in solid dosage form via oral route is often difficult on account of the bad taste of some active substances or some excipients contained in the medication and the much developed sense of smell and taste in animals. It has been observed in animals that the main reason which makes it difficult even impossible to properly follow oral treatment is the lack of palatability of the medication. The same applies to nutraceuticals or food supplements. Animal owners are particularly sensitive to the reactions of their animals when a composition needs to be taken. A composition given to an animal should be a source of pleasure shared by both owner and animal.

Appetency is defined as the psychological state corresponding to a desire to absorb a food or drink in response to the perceiving of the organoleptic characteristics of this product. The capacity to arouse appetency is called palatability. The combination of these characteristics determines the appeal of a product to be taken by oral route by animals that are fed normally. More particularly, the palatability of a medication plays a large part in the refusal or acceptance by an animal for spontaneous taking of treatment and for repeated taking thereof over sometimes long periods. Some treatments may have to be taken daily and even over a lifetime.

The palatability of a medicine, a nutraceutical or food supplement administered via oral route leads to the acceptance and voluntary ingestion thereof by an animal. This palatability can be measured by a general appetency test taking into account different parameters of the composition formulated in solid form, such as the spontaneous taking thereof from the hand or on the ground, or the consumption thereof even if it is given over several times or taken at regular intervals by the animal.

Texture is defined as a physical state corresponding to a formulation arranged in a certain manner by production technology. It is on texture that hardness, brittleness, softness, elasticity, colour of the composition all depend.

Regarding the parameters of shape or size, these facilitate taking hold of the composition or the absorption thereof at a single time.

In the prior art, numerous solutions, whether or not combining these two major parameters even the other parameters, have been proposed to facilitate the absorption of medication in particular by an animal.

Concerning appetency, several methods have been proposed:

One first option is to mask the unpleasant taste and/or smell of the constituent(s), chiefly one or more active substances, by the encapsulation or coating thereof.

The following patent applications: EP 0 997 143, EP 1 490 037, WO 01/15547, AU 2001279664, FR 2 350 105, U.S. Pat. Nos. 5,380,535, 3,037,911, describe how to encapsulate or coat one or more constituents and the techniques used.

These solutions require numerous encapsulation or coating steps, or have recourse to a production step such as extrusion which may degrade the fragile active substances or denature the constituents such as flavourings or palatable materials.

Another option to facilitate oral administration is to contain the composition, chiefly a medication, within a palatable material.

The following patent applications: FR 2 896 958, FR 2 715 803, U.S. Pat. Nos. 5,853,757, 6,143,316, 5,792,470, 5,674,515, EP 0 574 301, U.S. Pat. No. 4,857,333, DE 198 53 729, WO 03/030863, WO 2004/043427, WO 2007/090987, propose baits formed with palatable materials.

The disadvantage with these baits is that their use requires the handling namely the previous insertion of the medicine into the bait, which may deter some users and may also become tedious if a large number of animals are to be treated. In addition their large volume (necessarily larger than the medicinal product) requires a high amount of material and production must be adapted to their complex shape; these baits are therefore often costly.

A further option is to isolate the active substances in the centre of a matrix obtained by compressing the dry constituents, comprising a palatable substance to mask the taste and facilitate the taking and consumption thereof.

Patent application EP 0 320 320 describes a tablet for pet animal characterized in that it is formed of at least one core containing one or more active substances, fully contained within a matrix that is tasty for an animal. In such compositions it is the texture which amounts to the main drawback. A compressed or tablet form gives rise to hard forms scarcely appreciated by animals. In addition, the production of these types of core tablets entails numerous constraints to ensure full enclosing of the central part.

The following patent applications: EP 0 725 570, EP 0 725 627, propose compositions formed of two parts, a central part enclosing the constituents having an unpleasant taste and/or smell, and an outer part surrounding the central part. These are baits and the objective is to attract the animal so that by biting the composition the animal will be vaccinated. These have several disadvantages:

- when forming the matrix, an increase in temperature to obtain the fusing of some constituents is necessary to melt the polymer so that it is closely mixed, which may be highly restrictive to obtain the stability of the active substance;
- the producing of such matrixes is complex and costly;
- storage requires special conditions to guarantee the integrity of the dosage form.

Patent application FR 2 709 420 describes a shape and size for a tablet so that it can be more easily grasped by animals, cats in particular.

The following patent applications: IE 2004 0393, and GB 2 432 506, describe palatable pet chews obtained by extrusion or extrusion moulding. The main disadvantage of these items is that they are consumed for several minutes, even abandoned and then picked up again to be re-chewed before being consumed. It is therefore not possible to follow a treatment schedule with certainty.

Patent application US 2011/0183036 describes pet treats obtained by extrusion moulding. The main drawback with these treats is that their production requires heat at a temperature higher than 82° C., from an extruded-moulded paste and there is hence lack of weight regularity. In addition, this paste contains water of which part, between 3 and 15%, remains in the treat after it has been formed. The application describes a treat and not a medicinal product.

U.S. Pat. No. 6,455,083 describes edible chews obtained by extrusion-moulding. The main drawback is that they are thermoplastics i.e. polymerisation occurs in the extruder chiefly of the proteins with water (10 to 20%). Having regard to their texture, these items will not be absorbed at once but will be chewed with the risk of being abandoned. The patent describes nutritional chewable products and not medicinal products.

The following patent applications: FR 2 154 424, and U.S. Pat. No. 5,894,029 refer to the production of feed for pet animals. The production methods used are in no way adapted for the particular production of medicinal products. They may be highly harmful for the stability of the active substances, through the use of water in the formulas or processes, through the use of heat with or without pressure.

Patent application U.S. Pat. No. 5,637,313 describes special compositions, but more especially a particular method for obtaining coated tablets, namely the matrix after mixing is coiled into a cord of a certain diameter and cut to a certain length to obtain the desired weight. This production does not allow guaranteed full control over weight and hence over the quantity of active substance per unit, which is antinomic for a medicinal product.

Regarding texture, bearing in mind that it is strongly related to the composition and hence also to appetency, three main preparation methods have been proposed:

The first, the oldest, is dry compression to obtain tablets or pills. The patent applications already cited: EP 0 997 143, EP 1 490 037, EP 0 574 301, EP 0 320 320, U.S. Pat. Nos. 5,380,535, 3,037,911, FR 2 709 420 describe hard, dry forms scarcely appreciated by animals and numerous cases of rejection by animals have been reported.

The second, most recent, is the production of chewable tablets obtained by extrusion. For example the following patent applications: US 2004/0043925, US 2004/0037869, US 2001/036464, WO 2008/030469, WO 2005/013714, WO 89/12442, described extruded palatable forms having a relatively soft texture much appreciated by animals in particular pet animals such as dogs and cats. Having regard to the production mode, namely the use of an extruder, the matrix continually leaves the production line and is then cut to the desired length to obtain the required weight and hence a constant quantity of active substance(s) as required for a medicinal product. This requires perfect control over extrusion parameters. Unfortunately it is known that with this technique a variation in density of the extrudate cannot be ruled out which, at constant length, inevitably leads to a variation in weight. To overcome this possibility, the chewable tablets must be weighed one by one and those not conforming must be discarded since they cannot be recycled as the active substance may be modified by further extrusion. This technique proves to be in no way economical. To conclude, it would not be chosen by persons skilled in the art to produce a medicinal product or nutraceutical or food supplement in which the quantity of active substance(s) must be fully controlled.

Patent application US 2004/151759 describes chewable tablets obtained using conventional techniques: compressing dry granulated powder or extrusion with drying at 50° C. The two production methods have recourse to water for granulating, the water being removed before compression to obtain conventional tablets or after extrusion to obtain chewable tablets. These two techniques have the disadvantages already mentioned.

The third and last proposed is the production of soft tablets by moulding using equipment for pressing hamburgers, steaks, nuggets, cookies (before baking) (patty pressing machines). For example, the following patent applications: US 2005/0226908 and the patent applications in the same family, WO 2009/064859 and US 2009/0280159, WO 2012/049156, US 2012/0141574 describe chewable tablets obtained by moulding a paste with little or no pressure (explicit in applications WO 2009/064859, US 2009/0280159, US 2012/0141574), prepared with water (application WO 2012/049156) or in the presence of water (application US 2005/0226908), the use of heat (applications US 2005/0226908, WO 2012/049156) all the applications recommending the same equipment by Formax Corporation: Formax F6™. Having regard to the production mode, namely the use of patty pressing machines which are fed with a paste which may be homogeneous but is of random density which leads to a random moulded amount and hence to a random amount of active substance(s) not compatible with a medication. This requires full control over the physical characteristics of the paste. Unfortunately it is known that a variation in density cannot be ruled out with a scarcely fluid paste since it is cold moulded. In addition to this disadvantage is that of the system for feeding the moulds which aerates the paste, which inevitably leads to a variation in the weight of the tablets. To overcome this problem the chewable tablets must be weighed one by one, those not conforming not able to be recycled as the supply of active substance may be modified by further forming. This technique proves to be in no way economical. To conclude, it would not be chosen by persons skilled in the art to produce a medication or nutraceutical or food supplement for which the quantity of active substance(s) must be fully controlled.

The applicant has therefore set itself the objective of remedying the disadvantages of the prior art, of developing a composition and finding a process with which it is possible to impart improved palatability and an appreciated texture to compositions in solid form for oral administration to animals. In particular the applicant has endeavoured to develop a veterinary composition for simple oral administration adapted to and appreciated by every animal species, that is economical and whose production can easily be given industrial application, the quantity of each component being fully controlled in particular the active substance(s) if it is a medicinal product or nutraceutical or food supplement.

During the work which led to the development of the palatable composition of the invention, the applicant found that the obtaining of this palatable composition containing a maximum amount of palatable matter using the stock cube compression method intended in particular for compressing formulas with high fat content, led to veterinary compositions in solid form for oral administration containing one or more active substances well consumed by all animal species. With this technique it is possible to choose a composition that is fully adapted and hence appreciated by each targeted animal species, by proper selection of the formula components, the majority of which are sought to be palatable, the texture and shape and size being particular to the targeted animal species. With this technique it is also possible to select components for the composition that do not cause instability in particular degradation of the active substance or substances. This technique allows the production of very homogeneous compositions and guarantees with much accuracy the quantity of active substance(s) contained therein. In addition, this technique is most economical and can easily be given industrial application.

SUMMARY OF THE INVENTION

The invention relates to a solid composition, the use and preparation thereof, at least containing relative to the total weight of the composition:

- 5 to 30%, preferably 8 to 20% by weight of at least one fat chosen from among a liquid oil, fat, wax or mixture thereof, the liquid oil possibly representing more than 8% by weight of the composition;
- 0.001 to 85% by weight of at least one active substance; and
- 20 to 95%, preferably 40 to 70% by weight of at least one palatable material;
- the said composition being obtained by compressing a fluid homogeneous granular material having a particle size of between 50 and 1000 μm, preferably between 200 and 600 μm;
- the said compression technique giving compositions having a most homogeneous unit weight not differing by more than to within about 3% from the theoretical value of the required weight, and preferably not more than to within about 2% of the theoretical value of the required weight;
- for use as medicinal product, nutraceutical or food supplement, for oral administration to mammals other than man, in particular to domestic animals such as dogs cats or horses.

By « active substance» is meant a medicinal, nutraceutical or food supplement substance having a therapeutic effect or biological activity.

In the uses and compositions of the invention, the liquid oil is preferably selected from among vegetable oils such as olive oil, groundnut oil, rapeseed oil, sunflower oil and the mixtures thereof.

In the uses and compositions of the invention, the fat is preferably selected either in the animal kingdom or in the vegetable kingdom depending on the targeted animal species, from among pasty or hard fats such as chicken fat, duck fat, lard, tallow, butter, palm fat, palm stearin, margarine, palm oil optionally hydrogenated, hydrogenated coconut oil, cetyl palmitate, and the mixtures thereof.

In the uses and compositions of the invention, the wax is preferably chosen either in the animal kingdom or in the vegetable kingdom depending on the targeted animal species, from among beeswax, carnauba wax, candelilla wax, and the mixtures thereof.

In the uses and compositions of the invention, the palatable material is chosen either in the animal kingdom or in the vegetable kingdom depending on the targeted animal species, preferably from among meat, meat powder, fish powder, cheese powder, milk derivatives, liver powder, gelatine, the extracts of these animal substances or the derivatives thereof; beer yeast; vegetable fibres; vegetable products or by-products such as fenugreek, apple, carrot, fodder beet, sugar beet, thyme, alfalfa, sugar cane, and cereals such as oats, wheat, rice, corn, soy, their derivatives e.g. powders and mixtures thereof; sugar (sucrose) in all its forms, crystallised, powdered, glucose, invert sugar, molasses, honey and its derivatives; and the mixtures thereof; or in the mineral universe, salt (sodium chloride).

It will be understood that a liquid oil, fat and wax may also be palatable materials for animals.

The composition further comprises one or more additives preferably chosen either in the animal kingdom or in the vegetable kingdom depending on the targeted animal species, from among fillers, binders, solvents, flavourings, surfactants, flavour enhancers, sweeteners, antioxidants, chelating agents, preserving agents, colouring agents and pH regulators.

Preferably the filler is chosen from among maltodextrins; cyclodextrins; lactose; talc; silica; silicates; phosphates, cellulose powder; microcrystalline cellulose; mica and carbonates.

Preferably the binder is selected from among polyvinyl alcohol polymers, polyvinylpyrrolidone, the copolymers of vinylpyrrolidone and vinyl acetate, carboxymethylcellulose, the salts and derivatives thereof, alginic acid and its salts, zein, pectins, gum arabic, acacia gum, gum tragacanth, karaya gum, xanthan gum, carrageenans, pullulan polymers, agar polymers, starches and the derivatives thereof, carbomers, acrylic acid cross-linked with polyalkenyl ethers, polycarbophils, and the mixtures thereof.

Preferably the solvent is chosen from among ethanol, propylene glycol, glycerine, cetyl alcohol, polyethylene glycols and their derivatives, and the mixtures thereof.

Preferably the flavouring is chosen from among essential oils, terpene derivatives such as menthol, and the mixtures thereof.

Preferably the surfactant is chosen from among glycol esters such as glycerol monostearate, the esters of fatty acids and sorbitan, the esters of polyoxyethylenated fatty acids and sorbitan; polyoxyethylenated vegetable oils such polyoxyethylenated castor oils, polyoxyethylenated hydrogenated vegetable oils such as polyoxyethylenated hydrogenated castor oils; lecithin and its egg or soy derivatives such as phosphatidylcholine, hydrogenated phosphatidylcholine, lysophosphatidylcholine, hydrogenated lysophosphatidylcholine, and the mixtures thereof.

In one preferred embodiment, the flavour enhancer is sodium glutamate.

In one preferred embodiment, the sweetener is chosen from among aspartame; sodium saccharin; thaumatin; polyols such as sorbitol, xylitol, isomalt, maltitol, mannitol, and lactitol; and the mixtures thereof.

Preferably the antioxidant is chosen from among ascorbic acid, its salts and derivatives, sodium or potassium metabisulphite, sodium bisulphite, butylhydroxyanisol, butylhydroxytoluene, gallic acid and the derivatives thereof such as propyl gallate, and the mixtures thereof.

Preferably the chelating agent is chosen from among EDTA and its salts, tartaric acid and its salts, and the mixtures thereof.

Preferably the preserving agent is chosen from among parabens, benzoic acid, sodium benzoate, sorbic acid, potassium sorbate, and the mixtures thereof.

Preferably the colouring agent is chosen from among iron oxides, titanium oxide, curcumin, caramel, carotenes, and the mixtures thereof.

Preferably the pH regulator is chosen from among citric acid, its salts and derivatives, sodium carbonates, delta glucono lactone, and the mixtures thereof.

In one preferred embodiment, the additive(s) represent 0.01 to 75%, preferably 1 to 50% by weight of the composition relative to the total weight of the composition.

It will be understood that a filler may have several functions, therefore a vegetable product or by-product such as cereal powder or sugar may be both an inert filler and a palatable material.

Preferably, the active medicinal substance is chosen from among anti-infectives such as antibiotics and sulfonamides, cardiotonics; internal and external anti-parasitics; insecticides; insect growth inhibitors; anti-arthritics; anti-inflammatories whether or not steroidal; anti-histaminics; hormones such as prostaglandins; substances for digestive therapy such as gastro-intestinal dressings and sedatives, anti-ulcer agents and substitution flora; anti-diarrhoeals; hepato-protector agents; antispasmodics; laxatives; intestinal antiseptics; substances for respiratory therapy such as respiratory analeptics; antitussives, bronchodilators, bronchial and mucolytic fluidifiers, and respiratory antiseptics; substances acting on the nervous system such as analgesics, sedatives and tranquillisers; anti-epileptics; anaesthetics; orexigenics; anorexigenics, substances for immunity therapy such as interleukins and interferon in particular; substances for anticancer treatment such as antimitotics and cytostatic; macro-, micro-nutrients and trace elements; vitamins; extracts of plants or animal organs; and the mixtures thereof.

In one advantageous embodiment, the active substance is chosen from among antibiotics such as amoxicillin, clavulanic acid, cephalexin, rifaximin; anti-parasitics such as ivermectin, moxidectin, milbemycin pyrantel and its derivatives such as the pamoate, praziquantel, benzimidazoles, their salts or derivatives; insecticides such as fampronil; cardiotonics such as levosimendan; anti-arthritics such as diacerein.

Preferably the active nutraceutical substance or food supplement is chosen from among plant or animal organ extracts for their anti-infection, anti-bacterial, anti-fungal, anti-diarrhoeal, hepato-protector, anti-spasmodic, laxative, intestinal antiseptic activity; their action on respiratory problems such as coughs, as bronchodilators, bronchial and mucolytic fluidifiers, respiratory antiseptic, analgesic, sedative, tranquilliser, anti-arthritic, insecticide, anti-parasitic, anti-ulcer, anti-stress; and substitution flora; macro-, micro-nutrients and trace-elements; vitamins, and the mixtures thereof.

In one advantageous embodiment, the active nutraceutical or food supplement substance is chosen from among extracts of plants or animal organs for their anti-arthritic action such as chondroitin sulfate, chitosan and its derivatives; for their anti-ulcer and/or anti-stress action such as fermented soy extract; for their insecticidal or insect repellent action such as pyrethrums; vitamins such as vitamin C, vitamin D3; substitution flora such as *Enterococcus faecium*; micronutrients such as selenium provided by a strain of *Saccharomyces cerevisiae*.

It will be understood that an active substance may have several functions: for example fermented soy extract may be both an active substance and a palatable material.

DETAILED DESCRIPTION OF THE INVENTION

The detailed description given below is based in particular on examples given solely as an illustration and with reference to the appended drawings in which.

Figure 1:
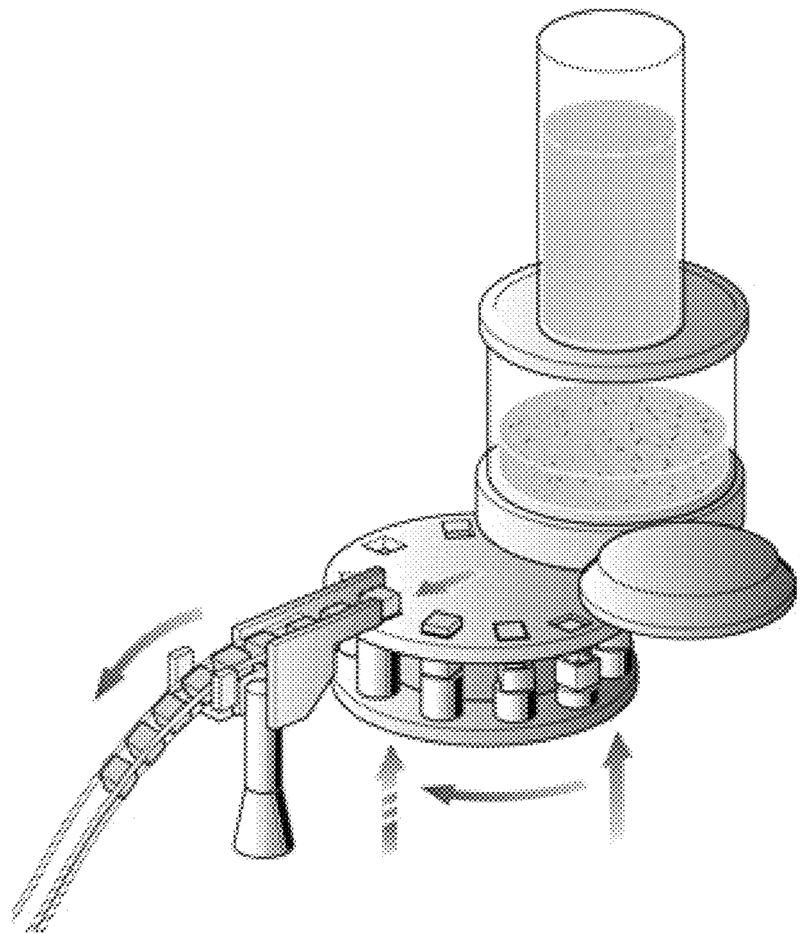
FIG. 1 is a schematic illustration of a stock cube press.

The present invention relates to the obtaining and use of palatable compositions in solid form with controlled dosage, obtained by compression, for oral administration to animals. The compositions have a texture, shape and size appreciated by animal species. The present invention is in the form of a tasty, perfectly dosed cube well accepted by all animals regardless of species and is rapidly absorbed whether given occasionally or on a repeat basis.

The compositions of the present invention are obtained by compression by means of a stock cube press intended in particular for the compressing of formulas with high fat content.

The compositions or «edible/chewable cubes» of the present invention are obtained by compression using a stock cube press not having recourse to any equipment operating continuously such as extruders or having recourse to a continuous production step such as extrusion-moulding, or working from a heterogeneous paste or mixture such as patty pressing machines, without or without the presence of heat or moisture.

This technique is widely used in the field of human food as shown in the following patent applications: U.S. Pat. No. 6,126,979, WO 2004/112513, WO 2006/063694, WO 2007/

085609, WO 2009/068378, OA 12967 describing compositions and the use of compression to form stock cubes or stock tablets. They cannot be used directly, and must first be dissolved in water or an aqueous vehicle that is preferably hot or at least tepid. In addition, these stock cubes are very friable since it must be possible to crumble them easily into food preparations. On this account, persons skilled in the art would not be prompted to use these formulations and their method of production to obtain a solid palatable composition having the desired texture.

The solid palatable compositions obtained are used for administration to animals for therapeutic treatment, either medicinal or nutraceutical or as food supplement, the animals more particularly being mammals.

The compositions of the present invention are typically in the form of cubes to be eaten/chewed used to facilitate oral dispensing to animals, preferably mammals.

Even if the palatable composition in solid form for oral administration to animals is called an «edible/chewable cube» it can have other shapes provided the constraints of the equipment are heeded, namely at least the top and bottom surfaces of the edible/chewable cube are planar.

The method for compressing stock cubes is known in the prior art, and is used in particular in the field of human food. These products are typically stock cubes. However, the compositions such as stock cubes obtained with this compression method have never been used up until now in the veterinary field i.e. applied, given directly to animals and more particularly mammals by direct oral administration, man only consuming these compositions indirectly either dissolved in hot or tepid water or crumbled onto food preparations.

Compared with other techniques for producing oral route products for animals as described in the prior art including in particular the compressing of dry powder, extrusion and moulding, the compressing of stock cubes allows products to be obtained that have a higher fat and palatable material content, which leads to perfect appetency i.e. total ingestion by animals even on a repeat basis. All the compositions contain an active substance, this compression method providing full control over the weight of the edible/chewable cube and hence over the quantity of active substance contained in each unit of the end product, thereby guaranteeing compliance with therapeutic treatment.

In the prior art methods:

- the compression of dry powder does not allow the obtaining of products sufficiently high in palatable materials, having a texture appreciated by animals;
- the extrusion and extrusion-moulding methods do not allow products to be produced that are sufficiently high in non-exuding fat, whilst obtaining perfect product dosage;
- the methods for moulding hamburgers do not allow products to be obtained that are sufficiently high in non-exuding fat whilst obtaining perfect product dosage.

Therefore, the products obtained by extrusion or moulding in particular generally have strong variations in weight. These variations are due to different factors such as the feeding of mixture to the equipment, but also the mixture itself in a paste formed in the screws of the extruder, or formed directly for moulding, this paste being highly heterogeneous. These variations can be offset by sorting the products leaving the production lines, but such sorting is associated with major loss of product leading to non-negligible additional costs. The calibration of the products is particularly determinant for compositions incorporating an active substance. To allow the administering of a constant quantity of active substance, the end product must be perfectly calibrated regarding weight. This calibration is advantageously obtained when producing the compositions of the present invention by compressing stock cubes.

The invention therefore relates to a process for producing an edible/chewable cube for animals comprising the following steps:

- placing the powder components, 0.001 to 55% by weight of at least one active substance, and 20 to 95%, preferably 40 to 70% by weight of at least one palatable material, optionally one or more additives, taking care to give preference to components having a fine particle size, less than 200 μm and preferably less than 100 μm, in a vertical mixer-granulator;
- mixing without providing any heat or water;
- adding the liquid components and optionally one or more liquid additives, components dissolved in a liquid fat or a liquid additive;
- adding the fats, a mixture of 5 to 30%, preferably 8 to 20% by weight of at least one fat chosen from among a liquid oil, a fat, wax or mixture thereof, the liquid oil not to represent more than 8% by weight of the edible/chewable cube:
- by vaporising fats liquid at ambient temperature, or
- by vaporising fats in a previously liquefied mass, or
- directly if the fats are in powder form of fine particle size, less than 200 μm and preferably less than 100 μm,
- under stirring until a dry, fluid homogenous granular material is obtained not having any agglomerates, and no clumping;
- calibrating the granular material at 600 μm;
- compressing the dry, fluid calibrated granular material using standard equipment such as stock cube presses by Fette or Bonals, (FIG. 1: schematic of the operating principle of the press) giving compact, homogeneous masses.

Figure 2:
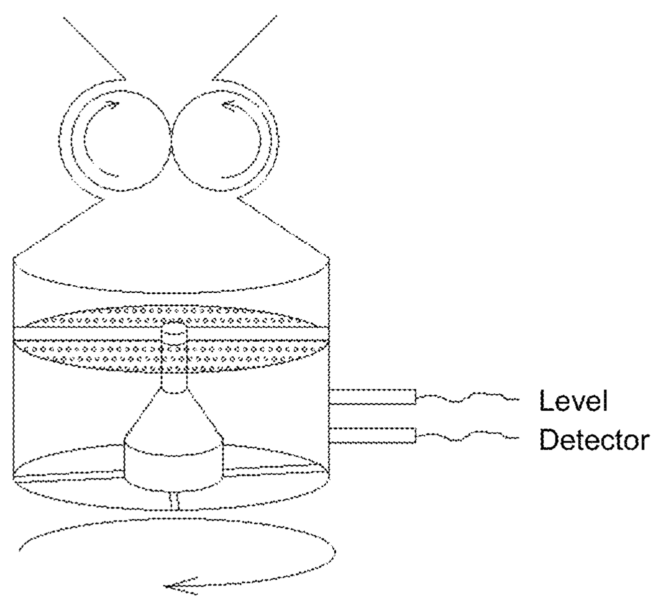
FIG. 2 is a schematic illustration of a cluster-breaker-size grader advantageously mounted on the feed vessel of the stock cube press.

The production equipment for implementing the above method is advantageously modified:

- by adding a cluster breaker/size grader to the feed vessel of the stock cube press, which will allow improved filling of the alveolus with a constant volume i.e. the volume of the granular material, hence the weight placed in the alveolus is as constant as possible to guarantee a very small variation in weight of the resulting edible/chewable cube relative to the fixed theoretical weight, with the consequence that the quantity of active substance contained in the cube will be fully constant (FIG. 2: cluster breaker/size grader); and
- to improve extraction of the edible/chewable cube, but also to prevent any heating which could be detrimental to the stability of the cube/active substance, the compression stage is chilled.

The hardness of the edible/chewable cubes can be controlled by adjusting the pressure applied by the stock cube press and the composition.

The said compression technique yields items having very homogeneous unit weight not differing to within about more than 3% of the theoretical value of the required weight, and preferably to within about 2% of the theoretical value of the required weight, which allows use thereof:

- as medicinal product for mammals, except man, in particular for domestic animals such as dogs, cats or horses; or
- as nutraceutical or food supplement for mammals, except man, in particular for domestic animals such as dogs, cats or horses.

By « oil» is meant a fat that is liquid at ambient temperature. In general, the oil is of vegetable origin although it may be of animal or mineral origin. Depending on the targeted species, preference will be given to oils of vegetable or animal origin.

According to the invention, the edible/chewable cube may contain an acceptable liquid oil having no degrading activity on the other chosen components, in particular the active substance.

Better diffusion of the liquid oil through the mass of components of the formula facilitates homogeneity and improves the appearance of the edible/chewable cube especially if the fat is replaced at least in part by liquid oil.

In the uses and compositions of the invention, the liquid oil is preferably chosen from among olive oil, groundnut oil, rapeseed oil, sunflower oil and the mixtures thereof.

By « fat» is meant matter containing one or more lipids.

In the uses and compositions of the invention the fat is chosen either from the animal kingdom or from the vegetable kingdom depending on the targeted animal species, from among paste or hard fats, chicken fat, duck fat, lard, tallow, butter, palm fat, palm stearin, margarine, palm oil optionally hydrogenated, cetyl palmitate, hydrogenated coconut oil, and the mixtures thereof.

By « waxes» is meant waxes permitted in foods and in particular in animal feed.

In the uses and compositions of the invention, the wax is preferably chosen either from the animal kingdom from in the vegetable kingdom depending on the targeted animal species, from among beeswax, carnauba wax, candelilla wax, and the mixtures thereof.

In the uses and compositions of the invention the liquid oils, fats or waxes will allow granulating of the homogeneous mixture of powder components.

It will be understood that a liquid oil, fat or wax may also be palatable materials for animals.

The compositions of the present invention comprise at least one palatable ingredient in high quantity contributing towards the organoleptic characteristics of the composition according to the invention and its appetency for animals.

Palatable materials for targeted animals are substances of animal or vegetable origin for example, powdered directly after treatment such as drying or dehydration, grinding, calibrating, but also after processing with the addition of other components to promote preservation for example. The palatable components are selected from among substances of choice which are highly tasty for the targeted species, in particular carnivorous pet animals such as dogs and cats and herbivorous animals e.g. horses.

In the uses and composition of the invention, the palatable material is chosen either from the animal kingdom or from the vegetable kingdom depending on the targeted animal species, preferably from among meat, meat powders, fish powders, cheese powders, milk derivatives, liver powder, gelatine, the extracts of these animal substances or their derivatives; beer yeast; vegetable fibres; vegetable products or by-products such as fenugreek, apple, carrot, fodder beet, sugar beet, thyme, alfalfa, sugar cane, and cereals such as oats, wheat, rice, corn, soy, their derivatives such as flours and the mixtures thereof; sugar (sucrose) in all its forms, crystallised, powdered, glucose, invert sugar, molasses, honey or its derivatives; and the mixtures thereof; or in the mineral kingdom, salt (sodium chloride).

The composition further comprises one or more additives preferably chosen either from the animal kingdom or from the vegetable kingdom depending on the targeted animal species, from among fillers, binders, solvents, flavourings, surfactants, taste enhancers, sweeteners, antioxidants, chelating agents, preserving agents, colouring agents and pH regulators.

Preferably the filler is chosen from among maltodextrins; cyclodextrins; lactose; talc; silica; silicates; phosphates, cellulose powder; microcrystalline cellulose; mica and carbonates.

Preferably the binder is chosen from among polyvinyl alcohol polymers, polyvinylpyrrolidone, the copolymers of vinylpyrrolidone and vinyl acetate, carboxymethylcellulose, its salts and derivatives, alginic acid and its salts, zein, pectins, gum arabic, acacia gum, gum tragacanth, karaya gum, xanthan gum, carrageenans, pullulan polymers, agar polymers, starches and the derivatives thereof, carbomers, acrylic acid cross-linked with polyalkenyl ethers, polycarbophils, and the mixtures thereof.

Preferably, the solvent is chosen from among ethanol, propylene glycol, glycerine, cetyl alcohol, polyethylene glycols and their derivatives, and the mixtures thereof.

A flavouring is an odorous ingredient of a certain substance (of synthetic or natural origin) which is only perceived by the sense of smell. It does produce any sensation on the organ of taste and therefore has no taste.

Preferably the flavouring is chosen from among essential oils, terpene derivatives such as menthol, and the mixtures thereof.

Preferably the surfactant is chosen from among glycol esters such as glycerol monostearate, the esters of fatty acid and sorbitan, the esters of polyoxyethylenated fatty acids and sorbitan; polyoxyethylenated vegetable oils such as polyoxyethylenated castor oils, polyoxyethylenated hydrogenated vegetable oils such as polyoxyethylenated hydrogenated castor oil; lecithin and its soy or egg derivatives such as phosphatidylcholine, hydrogenated phosphatidylcholine, lysophosphatidylcholine, hydrogenated lysophosphatidylcholine, and the mixtures thereof.

In one preferred embodiment, the taste enhancer is sodium glutamate.

In one preferred embodiment, the sweetener is chosen from among aspartame; sodium saccharin; thaumatin; polyols such as sorbitol, xylitol, isomalt, maltitol, mannitol, and lactitol; and the mixtures thereof.

Preferably the antioxidant is chosen from among ascorbic acid, its salts and derivatives, sodium or potassium metabisulphite, sodium bisulphite, butylhydroxyanisol, butylhydroxytoluene, gallic acid and its derivatives such as propyl gallate, and the mixtures thereof.

Preferably, the chelating agent is chosen from among EDTA and its salts, tartaric acid and its salts, and the mixtures thereof.

Preferably, the preserving agent is chosen from among parabens, benzoic acid, sodium benzoate, sorbic acid, potassium sorbate, and the mixtures thereof.

Preferably the colouring agent is chosen from among iron oxides titanium oxide, curcumin, caramel, carotenes, and the mixtures thereof.

Preferably, the pH regulator is chosen from among citric acid, its salts and derivatives, sodium carbonates, delta glucono lactone, and the mixtures thereof.

In one preferred embodiment, the additive(s) represent 0.01 to 75%, preferably 1 to 50% by weight of the composition relative to the total weight of the composition.

It will be understood that a filler may have several functions, for example a vegetable product or by-product such as a cereal powder or sugar may be both an inert filler and a palatable material.

By «active substance» is meant the substance of a medicinal product, a nutraceutical or food supplement having a therapeutic effect or biological activity.

The active substance or substances may be simply distributed within the edible cube or they may previously be encapsulated or coated using techniques known to those skilled in the art, to improve their stability or to increase masking of their smell or taste vis-à-vis the olfactory or taste senses of the animal, or distributed by vaporising a non-aqueous solution in a solvent or better still in the oil of the composition depending on the stability thereof in the solvent.

Preferably the active medicinal substance is chosen from among anti-infectives such as antibiotics and sulfonamides, cardiotonics; internal and external anti-parasitics; insecticides; insect growth inhibitors; anti-arthritics; anti-inflammatories whether or not steroidal; anti-histaminics; hormones such as prostaglandins; digestive therapy substances such as gastro-intestinal dressings and sedatives; anti-ulcer drugs and substitution flora; anti-diarrhoeals; hepato-protectors; antispasmodics; laxatives; intestinal antiseptics; substances for respiratory therapy such as respiratory analeptics; antitussives, broncho-dilatators, bronchial and mucolytic fluidifiers; substances acting on the nervous system such as analgesics, sedatives and tranquillisers; anti-epileptics; anaesthetics; orexigenics; anorexigenics; substances for immunity therapy such as interleukins and interferon in particular; substances for anticancer therapy such as antimitotics and cytostatics; macro-, micro-nutrients and trace elements; vitamins; extracts of plants or animal organs; and the mixtures thereof.

In one advantageous embodiment, the active substance is chosen from among antibiotics such as amoxicillin, clavulanic acid, cephalexin, rifaximin; anti-parasitics such as ivermectin, moxidectin, milbemycin pyrantel and its derivatives such as the pamoate, praziquantel, benzimidazoles, their salts or derivatives; insecticides such as fampronil; cardiotonics such as levosimendan; anti-arthritics such as diacerein.

Preferably the active nutraceutical or food supplement substance is chosen from among extracts of plants or animals for their anti-infectious, antibacterial, anti-fungal, anti-diarrhoeal, hepato-protector, anti-spasmodic, laxative, intestinal antiseptic activity; for their activity on respiratory problems such as coughs, as bronchodilators, bronchial and mucolytic fluidifiers, respiratory antiseptic, analgesic, sedative, tranquilliser, anti-arthritic, insecticidal, anti-parasitic, anti-ulcer, anti-stress agents; and substitution flora; macro-, micro-nutrients and trace elements; vitamins, and the mixtures thereof.

In one advantageous embodiment, the active nutraceutical or food supplement substance is chosen from among extracts of plants or animals for their anti-arthritic action such as chrondroitin sulfate acid, chitosan and its derivatives; for their anti-ulcer and/or anti-stress action such as fermented soy extract; for their insecticidal or insect repellent action such as pyrethrums; vitamins such as vitamin C, vitamin D3; substitution flora such as *Enterococcus faecium*; micro-nutrients such as selenium provided by a strain of *Saccharomyces cerevisiae.*

It will be understood that an active substance may have several functions; for example fermented soy extract may be both an active substance and a palatable material.

According to one preferred embodiment, the invention concerns:

i) A solid, palatable composition comprising, relative to the total weight of the composition:

5 to 30%, de preferably 8 to 20% by weight of at least one fat, chosen from among a liquid oil, a fat, wax or mixture thereof, the liquid oil not to represent more than 8% by weight of the composition;

0.001 to 85% by weight of at least one active substance; and 20 to 95%, preferably 40 to 70% by weight of at least one palatable material, for use thereof as medicinal product for oral administration to mammals, except man, in particular for pet animals such as dogs, cats or horses;

or:

ii) A solid, palatable composition comprising, relative to the total weight of the composition:

5 to 30%, de preferably 8 to 20% by weight of at least one fat, chosen from among a liquid oil, a fat, wax or mixture thereof, the liquid oil not to represent more than 8% by weight of the composition;

0.001 to 85% by weight of at least one active substance; and 20 to 95%, preferably 40 to 70% by weight of at least one palatable material for use thereof as nutraceutical or food supplement for oral administration to mammals, except man, such as dogs, cats or horses;

characterized in that:

a) the liquid oil is chosen from among olive oil, groundnut oil, rapeseed oil, sunflower oil, and the mixtures thereof;

b) the fat is chosen from among chicken fat, duck fat, lard, tallow, butter, palm fat, palm stearin, margarine, palm oil optionally hydrogenated, cetyl palmitate, hydrogenated coconut oil and the mixtures thereof;

c) the wax is chosen from among beeswax, carnauba wax, candelilla wax, and the mixtures thereof;

d) the palatable material is chosen from among meat, meat powders, fish powders, cheese powders, milk derivatives, liver powder, gelatine, extracts of these animal substances or their derivatives; beer yeast; vegetable fibres; vegetable products or by-products such as fenugreek, apple, carrot, fodder beet, sugar beet, thyme, alfalfa, sugar cane, cereals such as oats, wheat, rice, corn, soy, the derivatives thereof such as flours, and the mixtures thereof; crystallised, sugar, powder sugar (sucrose), glucose, invert sugar, molasses, honey and its derivatives, and the mixtures thereof, salt (sodium chloride); and e) the said solid composition is obtained by mixing the components, vaporising fats, calibrating the dry, fluid granular material, and compressing the granular material in a stock cube press, whereby the mixture is in the form of a dry, fluid, homogeneous granular material;

the dry, fluid granular material has a particle size of between 50 and 1000 μm, preferably between 200 and 600 μm;

the solid, palatable composition has a unit weight to within about 3 of the theoretical value of the required weight, and preferably to within about 2% of the theoretical value of the required weight.

Evidently, these examples are given solely to illustrate the subject of the invention and are in no way limiting thereof.

EXAMPLES

Example 1

Preparation of Edible/Chewable Cubes According to the Invention for Dogs

Edible/chewable cubes containing 68 μg ivermectin and 57.5 mg pyrantel in pamoate form according to the invention were prepared using the following composition:

| | |
|---|---|
| Ivermectin | 0.001236% |
| Pyrantel pamoate | 2.963636% |
| Rapeseed oil | 5.00% |
| Tallow | 10.00% |
| Beef meat | 40.30% |
| Soy flour | 28.132428% |
| Salt | 2.00% |
| Molasses | 8.00% |
| Glucono delta lactone | 3.30% |
| Potassium sorbate | 0.30% |
| Propyl gallate | 0.0005% |
| BHA | 0.0018% |
| Citric acid | 0.0004% |

Ivermectin was added as a pre-mixture obtained from ivermectin, rapeseed oil and antioxidants.

The beef meat, soy flour, potassium sorbate, salt, glucono delta lactone, citric acid and pyrantel pamoate were placed in a mixer and mixed.

The ivermectin pre-mixture, liquefied tallow and molasses were poured onto the homogeneous powder mixture and mixed until a dry, fluid homogeneous granular material was obtained.

The granular material was calibrated through a 600 μm mesh screen. Edible/chewable cubes of parallelepiped shape and size 13.95×13.95×25.0 mm were obtained by compression using a stock cube press.

All the edible cubes were weighed separately, their theoretical weight being 5.5 g.

No cube differed by more than 2% from the theoretical weight.

This would not have been possible using the techniques usually used, namely extrusion which is a continuous production technique, or moulding with a paste.

Determination of the ivermectin content for the 5 lightest edible/chewable cubes and the 5 heaviest showed that the mixture was perfectly homogeneous since the dosage values all lay within the dose range of theoretical dose permitted for medicinal products.

Example 2

Monadic Appetency Test with the Edible/Chewable Cubes

A cross-over appetency test of the edible/chewable cubes obtained in Example 1 was performed on thirty male and female adult dogs of varied races.

The dogs of small size up to 11 kg were given 1 cube, medium-size dogs of 11 to 22 kg were given 2 cubes and the large-size dogs were given 3 cubes. If there were several cubes they were given at the same time.

This was a monadic test conducted in individual boxes for ten minutes per dog. The following were measured:

- taking:
  - from the hand,
  - from the ground, or
  - not taken
- consumption
  - total,
  - partial, or
  - not eaten.

For each of these criteria the number of individual dogs is specified for the entire panel and per size category (small/medium/large).

The calculation of acceptability was based on the percentage number of dogs which ate the entire edible/chewable cube.

Taking:

| | small-size dogs | medium-size dogs | large-size dogs |
|---|---|---|---|
| From the hand | 10 | 10 | 10 |
| From the ground | 0 | 0 | 0 |
| Not taken | 0 | 0 | 0 |

Consumption:

| | small-size dogs | medium-size dogs | large-size dogs |
|---|---|---|---|
| Partial | 0 | 0 | 0 |
| Full | 10 | 10 | 10 |
| Not eaten | 0 | 0 | 0 |

There was total acceptability and consumption of the edible/chewable cubes according to the invention (100%).

Example 3

Comparative Homogeneity Test Between the Weights of the Edible/Chewable Cubes and Chewable Tablets Obtained by Extrusion Twenty edible/chewable cubes obtained according to the invention and conforming to Example 1 were taken consecutively from the production line and weighed.

A batch of chewable tablets was produced by extrusion having the following formula:

| | |
|---|---|
| Ivermectin | 0.001236% |
| Pyrantel pamoate | 2.963636% |
| Tallow | 2.5% |
| Beef meat | 42.0% |
| Soy flour | 30.932404% |
| Salt | 2.00% |
| Molasses | 8.00% |
| Propylene glycol | 5.0% |
| Glucono delta lactone | 3.30% |
| Potassium sorbate | 0.30% |
| Propyl gallate | 0.0005% |
| BHA | 0.0018% |
| Citric acid | 0.0004% |

Similarly, twenty tablets were taken consecutively from the product line and weighed.

The weights recorded for the two samples of twenty items are given in the following Table:

| N° of item | Chewable cube Weight in grams | Chewable tablet Weight in grams |
|---|---|---|
| 1 | 5.53 | 5.55 |
| 2 | 5.56 | 4.83 |
| 3 | 5.51 | 5.92 |
| 4 | 5.49 | 5.49 |
| 5 | 5.42 | 6.24 |
| 6 | 5.41 | 4.86 |
| 7 | 5.53 | 5.69 |
| 8 | 5.56 | 6.27 |
| 9 | 5.60 | 4.78 |
| 10 | 5.59 | 4.96 |
| 11 | 5.55 | 5.67 |
| 12 | 5.48 | 6.13 |

-continued

| N° of item | Chewable cube Weight in grams | Chewable tablet Weight in grams |
|---|---|---|
| 13 | 5.45 | 6.06 |
| 14 | 5.49 | 5.19 |
| 15 | 5.50 | 5.43 |
| 16 | 5.47 | 4.99 |
| 17 | 5.57 | 4.75 |
| 18 | 5.52 | 5.78 |
| 19 | 5.49 | 6.01 |
| 20 | 5.55 | 5.26 |
| Difference | <2% | >14% |

A large difference, higher than 14%, was observed between the extreme weights of the chewable tablets and the mean weight of the 20 chewable tablets obtained by extrusion as compared with the weight difference, less than 2%, found with the edible/chewable cubes obtained according to the invention.

These weight differences necessarily lead to a variation of at least the same magnitude in the quantities of active molecules contained in the chewable tablets. It cannot be envisaged to use the extrusion or moulding process for producing unit forms of medicinal products unless the chewable tablets are weighed one by one on leaving the conforming machine with the discarding of all those which do not come within the weight range guaranteeing a quantity of active molecules such as laid down by regulations on medications. If, as a first approach in the example given, only those chewable tablets were retained whose weight did not differ by more than 5 percent from the theoretical weight, only 6 of the chewable tablets out of the twenty produced would be retained i.e. 30% of the production which is not economical and without any guaranteed quantity of the active molecules contained in the chewable tablets having a weight close to or equivalent to the upper and lower weight limits for selection of the chewable tablets. Similarly it cannot be envisaged to extrude or mould the discarded chewable tablets a second time since the available active molecules would inevitably be modified and would lead to modification of the therapeutic activity.

Example 4

Preparation of Edible/Chewable Cubes According to the Invention for Horses

Edible/chewable cubes were prepared with the following composition:

| | |
|---|---|
| Fermented soy extract | 83% |
| Hydrogenated palm oil | 10% |
| Crystallised sugar | 6% |
| Titanium oxide | 0.9% |
| BHA | 0.1% |

The crystallised sugar, fermented soy extract, BHA and titanium oxide were mixed together and previously liquefied hydrogenated palm oil was sprayed onto the mixture. The granular material obtained was calibrated on a screen of mesh size 600 μm.

Edible/chewable cubes of parallelepiped shape and size L 31×23×10 mm were obtained by compression using a stock cube press.

All the edible/chewable cubes were weighed separately. No cube differed by more than 2 percent from the theoretical weight.

Example 5

Appetency Test with the Edible/Chewable Cubes of Example 4

An appetency test of the edible/chewable cubes obtained in Example 4 was conducted with several horse and pony owners and in a riding centre.

The edible/chewable cube was offered to the horse or pony on the outstretched hand.

Acceptability and consumption of the edible cubes were total (100%).

The behaviour of the animals towards this cube is to be pointed out. Several riders reported that the horses and ponies were greatly attracted by this edible/chewable cube in this shape and colour. As soon as the first had been eaten they looked for more, putting their noses to the riders' pockets from which the cubes had been taken.

Example 6

Preparation of Edible/Chewable Cubes According to the Invention for Dogs

Edible/chewable cubes of 3 g containing 68 μg ivermectin, 57 mg pyrantel in pamoate form and 57 mg praziquantel according to the invention were produced with the following composition:

| | |
|---|---|
| Coated ivermectin | 1.0% |
| Coated pyrantel pamoate | 6.0% |
| Coated praziquantel | 5.0% |
| Liver powder | 46.00% |
| Hard fat | 8.00% |
| Glycerine | 12.00% |
| PEG 4000 | 12.00% |
| Gelatine | 6.00% |
| Sugar | 3.54% |
| Sorbic acid | 0.40% |
| BHA | 0.04% |
| Propyl gallate | 0.02% |

The liver powder, PEG 4000, gelatine, sugar, sorbic acid, BHA, propyl gallate, granulated ivermectin, granulated pyrantel pamoate and granulated praziquantel were placed in a mixer and mixed.

The liquefied hard fat and glycerine were poured onto the homogeneous powder mixture. Mixing was continued until a dry, fluid, homogenous granular material was obtained.

The granular material was calibrated through a screen mesh size of 600 μm.

Edible/chewable cubes of parallelepiped shape and size 17×17×9.6 mm were obtained by compression using a stock cube press.

All the edible/chewable cubes were weighed separately, their theoretical weight being 3.0 g.

No cube differed by more than 2 percent from the theoretical weight.

The invention claimed is:

1. A process for preparing solid, palatable chewable cubes for domestic, bred, or wild animals, wherein each cube comprises:

a. 5 to 30% by weight of at least one fat substance selected from the group consisting of liquid oil, fat, and wax, or a mixture thereof, the liquid oil not representing more than 8% by weight of the cube;

b. 0.01 to 55% by weight of at least one active substance, wherein the active substance is homogeneous throughout the solid, palatable chewable cube;

c. 40 to 70% by weight of at least one palatable material;

d. optionally one or more additives selected from the group consisting of fillers, binders, solvents, flavourings, surfactants, taste enhancers, sweeteners, antioxidants, chelating agents, preserving agents, colouring agents, and pH regulators;

i) the liquid oil is selected from the group consisting of olive oil, groundnut oil, rapeseed oil, and sunflower oil, or mixtures thereof;

ii) the fat is selected from the group consisting of chicken fat, duck fat, lard, tallow, butter, palm fat, palm stearin, margarine, palm oil optionally hydrogenated, cetyl palmitate, and hydrogenated coconut oil, or mixtures thereof;

iii) the wax is selected from the group consisting of beeswax, carnauba wax, and candelilla wax, or mixtures thereof;

iv) the palatable material is selected from the group consisting of meat, meat powder, fish powder, cheese powder, milk derivatives, liver powder, gelatin, the extracts of these animal substances or the derivatives thereof, beer yeast, vegetable fibres, vegetable products or by-products, sugar (sucrose) in all its forms, crystallised, powdered, glucose, invert sugar, molasses, honey and its derivatives, and sodium chloride, or mixtures thereof;

v) and wherein the cubes have less than 2% weight difference between the extreme weights of the cubes and the mean weight of the cubes;

and in that the process comprises the following steps:

placing at least one powder component, at least one active substance, and at least one palatable material in a vertical mixer-granulator;

mixing without providing any heat or water;

optionally adding liquid components, the liquid components being dissolved in a liquid fat or a liquid additive;

1) adding at least one fat substance, after granulating the at least one fat substance into a powderized form at ambient temperature to a particle size of less than 200 μm, or directly if the said at least one fat substance is in powder form of fine particle size, less than 200 μm;

2) mixing and granulating until a dry, and homogenous granular material is obtained, the dry and homogeneous granular material not having any agglomerates, and no clumping;

3) milling and calibrating the dry, fluid granular material obtained after step 2) to obtain the granules having a particle size of between 50 and 1000 μm; and 4) compressing the dry, fluid calibrated granules obtained after step 3) using a stock cube press, collecting the solid, palatable chewable cube tablet obtained after step 4).

2. The process according to claim 1, wherein each of the cubes tablet comprises 8 to 20% by weight of said fat substance.

3. The process according to claim 1, wherein the animals are domestic animals.

4. The process according to claim 3, wherein the domestic animals are dogs, cats or horses.

5. The process according to claim 1, wherein the composition further comprises one or more additives selected from the group consisting of fillers, binders, solvents, flavourings, surfactants, taste enhancers, sweeteners, antioxidants, chelating agents, preserving agents, colouring agents, and pH regulators.

6. The process according to claim 5, wherein the filler is selected from the group consisting of maltodextrins; cyclodextrins; lactose; talc; silica; silicates; phosphates, cellulose powder; microcrystalline cellulose; mica; and carbonates.

7. The process according to claim 5, wherein the binder is selected from the group consisting of polyvinyl alcohol polymers, polyvinylpyrrolidone, the copolymers of vinylpyrrolidone and vinyl acetate, carboxymethylcellulose, its salts and derivatives, alginic acid and its salts, zein, pectins, gum arabic, acacia gum, gum tragacanth, karaya gum, xanthan gum, carrageenans, gelatine, pullulan polymers, agar polymers, starches and their derivatives, carbomers, acrylic acid crosslinked with polyalkenyl ethers, polycarbophils, and mixtures thereof.

8. The process according to claim 5, wherein the solvent is selected from the group consisting of ethanol, glycol propylene, glycerine, cetyl alcohol, polyethylene glycols and their derivatives, and mixtures thereof.

9. The process according to claim 5, wherein the flavouring is selected from the group consisting of essential oils, terpene derivatives, and mixtures thereof.

10. The process according to claim 5, wherein the surfactant is a glycol ester, an ester of a fatty acid and sorbitan, an ester of polyoxyethylenated fatty acid and sorbitan, a polyoxyethylenated vegetable oil, a polyoxyethylenated hydrogenated vegetable oil, lecithin, a soy derivative of lecithin, or an egg derivative of lecithin.

11. The process according to claim 5, wherein the taste enhancer is sodium glutamate.

12. The process according to claim 5, wherein the sweetener is selected from the group consisting of aspartame; sodium saccharin; thaumatin; polyols; and mixtures thereof.

13. The process according to claim 5, wherein the antioxidant is selected from the group consisting of ascorbic acid, its salts and derivatives, sodium or potassium metabisulphite, sodium bisulphite, butylhydroxyanisol, butylhydroxytoluene, gallic acid and its dertivatives, and mixtures thereof.

14. The process according to claim 5, wherein the chelating agent is selected from the group consisting of EDTA and its salts, tartaric acid and its salts, and mixtures thereof.

15. The process according to claim 5, wherein the preserving agent is selected from the group consisting of parabens, benzoic acid, sodium benzoate, sorbic acid, potassium sorbate, and mixtures thereof.

16. The process according to claim 5, wherein the colouring agent is selected from the group consisting of iron oxides, titanium oxide, curcumin, caramel, carotenes, and mixtures thereof.

17. The process according to claim 5, wherein the pH regulator is selected from the group consisting of citric acid, its salts and derivatives, sodium carbonates, delta glucono lactone, and mixtures thereof.

18. The process according to claim 1, wherein the active substance is selected from the group consisting of anti-infectives, cardiotonics, internal and external anti-parasitics, insecticides, insect growth inhibitors, anti-arthritics, anti-inflammatories whether or not steroidal, anti-histaminics, hormones, substances for digestive therapy, anti-ulcer agents and substitution flora, anti-diarrhoeals, hepato-protectors, antispasmodics, laxatives, intestinal antiseptics, substances for respiratory therapy, antitussives, bronchodilators, bronchial and mucolytic fluidifiers and respiratory antiseptics, substances acting on the nervous system, sedatives and tranquillisers, anti-epileptics, anaesthetics, orexigenics, anorexigenics, substances for immunity therapy, substances for anticancer therapy, macro-, micro-nutrients and trace elements, vitamins, plant extracts, extracts from animal organs, and mixtures thereof.

19. The process according to claim 1, wherein the active substance is selected from the group consisting of antibiotics, clavulanic acid, cephalexin, rifaximin, anti-parasitics, moxidectin, milbemycin, pyrantel and its derivatives, praziquantel, benzimidazoles, their salts or derivatives, insecticides, cardiotonics, and anti-arthritics.

20. The process according to claim 1, wherein the active substance is selected from the group consisting of plant extracts, animal extracts, substitution flora, macro-, micronutrients and trace-elements, and mixtures thereof.

21. The process according to claim 1, wherein the active substance is selected from the group consisting of animal extracts for their anti-arthritic action, chitosan and its derivatives; for their anti-ulcer and/or anti-stress action; for their insecticidal or insect repellant action, substitution flora, and micro-nutrients.

22. The process according to claim 1, wherein said powder components have a particle size of less than 100 μm.

23. The process according to claim 1, wherein each of the cubes tablet is in the form of a compact mass with at least the top and bottom surfaces being planar surfaces.

24. The process according to claim 1, wherein the stock cube press is equipped with a cluster-breaker/size grader.

25. The process according to claim 1, wherein the stock cube press is equipped with a chilled compression stage.

26. The process according to claim 1, wherein the vegetable product or by-product is fenugreek, apple, carrot, fodder beet, sugar beet, thyme, alfalfa, sugar cane, or cereal.

27. The process according to claim 26, wherein the cereal is oats, wheat, rice, corn, soy, their derivatives, or mixtures thereof.

28. The process according to claim 1, wherein the sugar is crystallised, powdered, glucose, invert sugar, molasses, or honey and its derivatives.

29. The process according to claim 1, wherein the powder components further include one or more additives.

30. The process according to claim 1, wherein the liquid components further include one or more liquid additives.

* * * * *